US008197835B2

(12) United States Patent
Dietze et al.

(10) Patent No.: US 8,197,835 B2
(45) Date of Patent: Jun. 12, 2012

(54) BIOMEDICAL FOAM ARTICLES

(75) Inventors: Melita Dietze, Erkrath (DE); Burkhard Fugmann, Ratingen (DE); Michael Mager, Leverkusen (DE); Thorsten Rische, Unna (DE); Michael Heckes, Krefeld (DE); Daniel Rudhardt, Köln (DE); Rolf Gertzmann, Leverkusen (DE)

(73) Assignees: Bayer Innovation GmbH, Dusseldorf (DE); Bayer Materialscience AG, Leverkusen (DE)

( * ) Notice: Subject to any disclaimer, the term of this patent is extended or adjusted under 35 U.S.C. 154(b) by 634 days.

(21) Appl. No.: 12/296,380

(22) PCT Filed: Apr. 5, 2007

(86) PCT No.: PCT/EP2007/003077
§ 371 (c)(1),
(2), (4) Date: Feb. 27, 2009

(87) PCT Pub. No.: WO2007/115781
PCT Pub. Date: Oct. 18, 2007

(65) Prior Publication Data
US 2009/0169486 A1 Jul. 2, 2009

(30) Foreign Application Priority Data
Apr. 8, 2006 (DE) .......................... 10 2006 016 636

(51) Int. Cl.
*A01N 25/08* (2006.01)
(52) U.S. Cl. ........................................ 424/409; 514/945
(58) Field of Classification Search .................. None
See application file for complete search history.

(56) References Cited

U.S. PATENT DOCUMENTS

| 4,108,814 A | | 8/1978 | Reiff et al. | |
|---|---|---|---|---|
| 4,147,680 A | * | 4/1979 | Reischl et al. | ................ 521/163 |
| 4,664,662 A | | 5/1987 | Webster | |
| 4,791,149 A | | 12/1988 | Pocknell | |
| 5,395,318 A | * | 3/1995 | Kaprelian | ..................... 604/520 |
| 5,684,081 A | | 11/1997 | Dannhorn et al. | |
| 6,605,666 B1 | | 8/2003 | Scholz et al. | |
| 2003/0215358 A1 | * | 11/2003 | Schulman et al. | .............. 422/56 |
| 2004/0034162 A1 | | 2/2004 | Laas et al. | |
| 2004/0224622 A1 | * | 11/2004 | Sakurai et al. | ................ 451/526 |

FOREIGN PATENT DOCUMENTS

| EP | 0 171 268 | 2/1986 |
|---|---|---|
| JP | 11-228811 | 8/1999 |
| WO | WO/2004/037307 | 5/2004 |
| WO | WO 2007/115696 | 10/2007 |

OTHER PUBLICATIONS

European Committee for Standardization (CEN), "Test Methods for Primary Wound Dressings. Part 1: Aspects of Absorbency," European Standard, Mar. 2002, DIN EN 13726-1.
European Committee for Standardization (CEN), "Test Methods for Primary Wound Dressings. Part 2: Moisture Vapour Transmission Rate of Permeable Film Dressings," European Standard, Mar. 2002, DIN EN 13726-2.
European Committee for Standardization (CEN), "Paints, Varnishes and Plasitcs—Determination of Non-Volatile-Matter Content," European Standard, Feb. 2008, DIN EN ISO 3251.
European Committee for Standardization (CEN), "Binders for Paints and Varnishes—Polyisocyanate Resins—Genera Methods of Test," European Standard, Feb. 2007, DIN EN ISO 11909.
V.N. Anisimov et al., "Penopoliuretanovaya povyaska 'SAREL' v chirurgii ('SAREL' polyurethane foam dressing in surgery)", NGMA, Nischni Novogorod, 2003, p. 48.
Russian Office Action dated Apr. 29, 2011 based on Russian Application No. 2008 143 908 with English Language Translation.
International Search Report dated May 21, 2008 (8 pages).
Maassen, Dieter et al., "Polyalkylenglykole," Verlag Chemie, pp. 31-38, 1980.
Bailey, Frederick et al., "Polyoxyalkylenes,"Wiley-VCH Verlag GmbH, 2005, pp. 1-12.

* cited by examiner

*Primary Examiner* — James Rogers
(74) *Attorney, Agent, or Firm* — Baker Donelson Bearman Caldwell & Berkowitz, PC

(57) ABSTRACT

The present invention relates to biomedical foam articles for the wound sector which are formed by spraying a polymeric dispersion onto a wound. The polymeric dispersion being sprayed onto a wound surface forms a three-dimensional body which conforms to the spatial shape of the wound and which, as well as covering the wound surface, ensures a complete and accurately fitted packing of the wound in the depth dimension as well as the other dimensions. The biomedical foam articles of the present invention are particularly useful for treating chronic wounds.

18 Claims, No Drawings

BIOMEDICAL FOAM ARTICLES

CROSS REFERENCE TO RELATED APPLICATIONS

This application is a §371 National Stage Application of PCT/EP2007/003077 filed Apr. 5, 2007 which claims priority to German Application 10 2006 016 636.1 filed Apr. 8, 2006.

BACKGROUND OF THE INVENTION

1. Field of the Invention

The present invention relates to biomedical foam articles for the wound sector which are formed by spraying a polymer onto a wound. The polymer being sprayed onto a wound surface forms a three-dimensional body which conforms to the spatial shape of the wound and which, as well as covering the wound surface, ensures a complete and accurately fitted packing of the wound in the depth dimension as well as the other dimensions, and also has highly absorbent properties. The biomedical foam articles of the present invention are particularly useful for treating chronic wounds.

2. Description of Related Art

A chronic wound is any wound which has not epithelialized within a physiological healing time of 2-3 weeks. The most frequent forms of chronic wounds by far are decubitus ulcers (caused by chronic pressure), chronic venous ulcers of the legs (caused by chronic venous insufficiency) and diabetic ulcers (caused by angiopathy and neuropathy).

The standard treatment of chronic wounds follows the principle of "moist wound healing" with different wound contact materials. The typical materials of moist wound treatment are placed in the form of bonded fibrous nonwoven webs on the wound to obtain optimal wound covering and, by maintaining the moist wound environment, to speed wound healing.

However, extending conventional treatment methods to chronic wounds has the disadvantage that conventional wound contact materials merely cover the wound surface, but do not pack the wound three-dimensionally (especially not depthwise), which can lead to deficiencies in relation to exudate handling, a heightened risk of infection but also increased maceration at the wound edges.

The absence of wound packing in the case of cavity wounds for example can lead to exudate collecting on the floor of the wound, which as well as hindering wound healing also leads to a softening of the healthy tissue at the wound edge and ultimately to maceration. The presence of excess exudate further favours the genesis of infections.

EP 171 268 B1 discloses a wound dressing comprising a multiplicity of pieces of an absorbent material contained within a porous bag. However, such a wound dressing has one disadvantage in that it does not always lead to an accurately fitted packing of the wound in the depth dimension as well as the other dimensions. Furthermore, such a wound dressing is complicated to handle and may be difficult to keep sterile.

DE 36 38 379 discloses a method of making a medical wound dressing based on a room temperature curing, two-component polyorganosiloxane composition which gives an elastic polysiloxane foam material capable of conforming to the contours of a wound. However, the polysiloxane foam material thus formed is not highly absorbent and therefore cannot be used for wounds which secrete large amounts of wound fluid.

There is therefore a need for a novel wound contact material which optimally conforms to the often deep and/or complex wound shapes typical of many chronic wounds because its shape adapts in area and depth. Furthermore, such a wound contact material should be simple and hygienic to apply and preferably also develop an effect which is antibacterial, pain alleviating and/or wound healing accelerating. Further important properties are rapid curing and also a sufficient liquid imbibition (absorption) on the part of the material forming the wound contact material.

A prerequisite for an effective use is rapid curing (i.e. solidification of the liquid polymer to a solid foam article, determined by sensory monitoring of the viscosity) of the biomedical foam article within not more than five minutes, preferably not more than 2 minutes, more preferably not more than one minute and most preferably less than 30 seconds.

A further prerequisite is a physiological saline absorbence of 100 to 2500%, preferably 100% to 2000%, more preferably 100 to 1500% and most preferably 300 to 1500% (determined according to DIN EN 13726-1 Part 3.2) and also a water vapour transmission rate of 2000 to 12 000 g/m$^2$ per 24 h, preferably 3000 to 10 000 g/m$^2$ per 24 h and more preferably 3000 to 5000 g/m$^2$ per 24 h (determined according to DIN EN 13726-2 Part 3.2). This requires that the foam have at least some open-cell content.

SUMMARY OF THE INVENTION

It has now been found that, surprisingly, this object is achieved by the biomedical foam articles of the present invention which are described hereinbelow.

The present invention accordingly provides in a first aspect a biomedical foam article comprising a porous material having at least some open-cell content and needing not more than five minutes, preferably not more than 2 minutes, more preferably not more than one minute and most preferably less than 30 seconds, to cure from a liquid form into a solid foam article.

DETAILED DESCRIPTION OF A PREFERRED EMBODIMENT

Preferably, such a biomedical foam article additionally has a physiological saline absorbence of 100 to 2500%, more preferably 100% to 2000%, even more preferably 100 to 1500% and in particular of 300 to 1500% (determined according to DIN EN 13726-1 Part 3.2).

Moreover, such a biomedical foam article preferably additionally has a water vapour transmission rate of 2000 to 12 000 g/m$^2$ per 24 h, more preferably 3000 to 10 000 g/m$^2$ per 24 h and most preferably 3000 to 5000 g/m$^2$ per 24 h (determined according to DIN EN 13726-2 Part 3.2).

The present invention further provides a biomedical foam article obtainable by spraying a composition comprising at least one ionic polymeric dispersion or emulsion and also at least one coagulant and also, optionally, at least one active component selected from the group consisting of broad-band antibiotics, antiseptics, antivirals, antifungals, antipathogenic peptides, local anaesthetics, non-steroidal anti-inflammatories, opiates and haemostatic, wound-healing, granulation-promoting actives, onto a substrate.

Human or animal skin having one or more wound sites is a preferred substrate.

The advantages of a sprayed application reside in particular in product handling. Application of a ready-made solution from a sterile spray can obviates the unpacking, cutting to size and placing of conventional materials; that is, application can even be carried out by the patient himself or herself, speeds the operation of dressing change, and is more hygienic, since direct manual contact with the wound during dressing change is obviated.

Preference is given to ionic polymeric dispersions having an aqueous medium as continuous phase.

Suitable ionic polymeric dispersions of the aforementioned kind are for example ionic rubber latex dispersions, ionic polyurethane dispersions, dispersions of ionic (meth) acrylate copolymers and dispersions of naturally occurring ionic biopolymers based on carbohydrate such as cellulose derivatives, for example cellulose acetate phthalate (CAP), cellulose acetate succinate (CAS), cellulose acetate trimelitate (CAT), hydroxypropylmethylcellulose phthalate (HP-MCP), carboxymethylcellulose (CMC), chitosan, as well as chitin, hyaluronan, dextrin, cellulose or starch and also further natural biopolymers such as, for example, lignin or casein.

Suitable (meth)acrylate copolymer is preferably a (meth) acrylate copolymer formed from 40% to 95% by weight of free-radically polymerized $C_1$- to $C_4$-alkyl esters of acrylic or methacrylic acid and containing 5% to 60% by weight of (meth)acrylate monomers having an anionic group in the alkyl radical. The (meth)acrylate copolymer consists of free-radically polymerized $C_1$- to $C_4$-alkyl esters of acrylic or methacrylic acid to an extent in the range from 40% to 100%, preferably 45% to 99% and in particular 85% to 95% by weight, and can contain 0% to 60%, preferably 1% to 55% and in particular 5% to 15% by weight of (meth)acrylate monomers having an anionic group in the alkyl radical.

In general, the proportions mentioned sum to 100% by weight. However, small amounts from 0% to 10%, for example 1% to 5%, by weight of further vinylically copolymerizable monomers, for example hydroxyethyl methacrylate or hydroxyethyl acrylate, may additionally be included without this leading to an impairment or change in the essential properties.

Preferred ionic polymeric dispersions are aqueous ionic polyurethane dispersions, aliphatic polyurethane dispersions and also polyurethane hybrid emulsions. Particularly preferred polymeric dispersions are aqueous anionic hydrophilic polyurethane dispersions.

Very particular preference is given to aqueous anionic hydrophilic polyurethane dispersions obtainable by
A) isocyanate-functional prepolymers being prepared from
   A1) organic polyisocyanates
   A2) polymeric polyols having number average molecular weights in the range from 400 to 8000 g/mol, preferably in the range from 400 to 6000 g/mol and more preferably in the range from 600 to 3000 g/mol and OH functionalities in the range from 1.5 to 6, preferably in the range from 1.8 to 3 and more preferably in the range from 1.9 to 2.1, and
   A3) optionally hydroxyl-functional compounds having molecular weights in the range from 62 to 399 g/mol, and
   A4) optionally isocyanate-reactive, anionic or potentially anionic and/or optionally nonionic hydrophilicizing agents,
   and
B) their free NCO groups then being wholly or partly reacted
   B1) optionally with amino-functional compounds having molecular weights in the range from 32 to 400 g/mol, and
   B2) with isocyanate-reactive, preferably amino-functional, anionic or potentially anionic hydrophilicizing agents
by chain extension, and the prepolymers being dispersed in water before, during or after step B), any potentially ionic groups present being converted into the ionic form by partial or complete reaction with a neutralizing agent.

To achieve anionic hydrophilicization, A4) and/or B2) shall utilize hydrophilicizing agents that have at least one NCO-reactive group such as amino, hydroxyl or thiol groups and additionally have —$COO^-$ or —$SO_3^-$ or $PO_3^{2-}$ as anionic groups or their wholly or partly protonated acid forms as potentially anionic groups.

Preferred aqueous, anionic polyurethane dispersions (I) have a low degree of hydrophilic anionic groups, preferably from 0.1 to 15 milliequivalents per 100 g of solid resin.

To achieve good sedimentation stability, the number average particle size of the specific polyurethane dispersions is preferably less than 750 nm and more preferably less than 500 nm, determined by laser correlation spectroscopy.

The ratio of NCO groups of compounds of component A1) to NCO-reactive groups such as amino, hydroxyl or thiol groups of compounds of components A2) to A4) is in the range from 1.05 to 3.5, preferably in the range from 1.2 to 3.0 and more preferably in the range from 1.3 to 2.5 to prepare the NCO-functional prepolymer.

The amino-functional compounds in stage B) are used in such an amount that the equivalent ratio of isocyanate-reactive amino groups of these compounds to the free isocyanate groups of the prepolymer is in the range from 40 to 150%, preferably between 50 to 125% and more preferably between 60 to 120%.

Suitable polyisocyanates for component A1) include the well-known aromatic, araliphatic, aliphatic or cycloaliphatic polyisocyanates of an NCO functionality of $\geq 2$.

Examples of such suitable polyisocyanates are 1,4-butylene diisocyanate, 1,6-hexamethylene diisocyanate (HDI), isophorone diisocyanate (IPDI), 2,2,4 and/or 2,4,4-trimethylhexamethylene diisocyanate, the isomeric bis(4,4'-isocyanatocyclohexyl)methanes or their mixtures of any desired isomer content, 1,4-cyclohexylene diisocyanate, 1,4-phenylene diisocyanate, 2,4- and/or 2,6-tolylene diisocyanate, 1,5-naphthalene diisocyanate, 2,2'- and/or 2,4'- and/or 4,4'-diphenyl-methane diisocyanate, 1,3- and/or 1,4-bis(2-isocyanatoprop-2-yl)benzene (TMXDI), 1,3-bis(isocyanatomethyl)benzene (XDI), and also alkyl 2,6-diisocyanatohexanoates (lysine diisocyanates) having $C_1$-$C_8$-alkyl groups.

As well as the aforementioned polyisocyanates, it is also possible to use, proportionally, modified diisocyanates of uretdione, isocyanurate, urethane, allophanate, biuret, iminooxadiazinedione and/or oxadiazinetrione structure and also non-modified polyisocyanate having more than 2 NCO groups per molecule, for example 4-isocyanatomethyl-1,8-octane diisocyanate (nonane triisocyanate) or triphenylmethane 4,4',4"-triisocyanate.

Preferably, the polyisocyanates or polyisocyanate mixtures of the aforementioned kind have exclusively aliphatically and/or cycloaliphatically attached isocyanate groups and an average NCO functionality in the range from 2 to 4, preferably in the range from 2 to 2.6 and more preferably in the range from 2 to 2.4 for the mixture.

It is particularly preferable for A1) to utilize 1,6-hexamethylene diisocyanate, isophorone diisocyanate, the isomeric bis(4,4'-isocyanatocyclohexyl)methanes, and also mixtures thereof.

A2) utilizes polymeric polyols having a number average molecular weight $M_n$ in the range from 400 to 8000 g/mol, preferably from 400 to 6000 g/mol and more preferably from 600 to 3000 g/mol. These preferably have an OH functionality in the range from 1.5 to 6, more preferably in the range from 1.8 to 3 and most preferably in the range from 1.9 to 2.1.

Such polymeric polyols are the well-known polyurethane coating technology polyester polyols, polyacrylate polyols, polyurethane polyols, polycarbonate polyols, polyether polyols, polyester polyacrylate polyols, polyurethane polyacrylate polyols, polyurethane polyester polyols, polyurethane polyether polyols, polyurethane polycarbonate polyols and polyester polycarbonate polyols. These can be used in A2) individually or in any desired mixtures with one another.

Such polyester polyols are the well-known polycondensates formed from di- and also optionally tri- and tetraols and di- and also optionally tri- and tetracarboxylic acids or hydroxy carboxylic acids or lactones. Instead of the free polycarboxylic acids it is also possible to use the corresponding polycarboxylic anhydrides or corresponding polycarboxylic esters of lower alcohols for preparing the polyesters.

Examples of suitable diols are ethylene glycol, butylene glycol, diethylene glycol, triethylene glycol, polyalkylene glycols such as polyethylene glycol, also 1,2-propanediol, 1,3-propanediol, butanediol(1,3), butanediol(1,4), hexanediol(1,6) and isomers, neopentyl glycol or neopentyl glycol hydroxypivalate, of which hexanediol(1,6) and isomers, neopentyl glycol and neopentyl glycol hydroxypivalate are preferred. Besides these it is also possible to use polyols such as trimethylolpropane, glycerol, erythritol, pentaerythritol, trimethylolbenzene or trishydroxyethyl isocyanurate.

Useful dicarboxylic acids include phthalic acid, isophthalic acid, terephthalic acid, tetrahydrophthalic acid, hexahydrophthalic acid, cyclohexanedicarboxylic acid, adipic acid, azelaic acid, sebacic acid, glutaric acid, tetrachlorophthalic acid, maleic acid, fumaric acid, itaconic acid, malonic acid, suberic acid, 2-methylsuccinic acid, 3,3-diethyl glutaric acid and/or 2,2-dimethylsuccinic acid. The corresponding anhydrides can also be used as a source of an acid.

When the average functionality of the polyol to be esterified is > than 2, monocarboxylic acids, such as benzoic acid and hexanecarboxylic acid can be used as well in addition.

Preferred acids are aliphatic or aromatic acids of the aforementioned kind. Adipic acid, isophthalic acid and optionally trimellitic acid are particularly preferred.

Hydroxy carboxylic acids useful as reaction participants in the preparation of a polyester polyol having terminal hydroxyl groups include for example hydroxycaproic acid, hydroxybutyric acid, hydroxydecanoic acid, hydroxystearic acid and the like. Suitable lactones include caprolactone, butyrolactone and homologues. Caprolactone is preferred.

A2) may likewise utilize hydroxyl-containing polycarbonates, preferably polycarbonate diols, having number average molecular weights $M_n$ in the range from 400 to 8000 g/mol and preferably in the range from 600 to 3000 g/mol. These are obtainable by reaction of carbonic acid derivatives, such as diphenyl carbonate, dimethyl carbonate or phosgene, with polyols, preferably diols.

Examples of such diols are ethylene glycol, 1,2-propanediol, 1,3-propanediol, 1,3-butanediol, 1,4-butanediol, 1,6-hexanediol, 1,8-octanediol, neopentyl glycol, 1,4-bishydroxymethylcyclohexane, 2-methyl-1,3-propanediol, 2,2,4-trimethyl-1,3-pentanediol, dipropylene glycol, polypropylene glycols, dibutylene glycol, poly-butylene glycols, bisphenol A and lactone-modified diols of the aforementioned kind.

The polycarbonate diol preferably contains 40% to 100% by weight of hexanediol, preference being given to 1,6-hexanediol and/or hexanediol derivatives. Such hexanediol derivatives are based on hexanediol and have ester or ether groups as well as terminal OH groups. Such derivatives are obtainable by reaction of hexanediol with excess caprolactone or by etherification of hexanediol with itself to form di- or trihexylene glycol.

In lieu of or in addition to pure polycarbonate diols, polyether-polycarbonate diols can also be used in A2).

Hydroxyl-containing polycarbonates preferably have a linear construction.

A2) may likewise utilize polyether polyols.

Useful polyether polyols include for example the well-known polyurethane chemistry polytetramethylene glycol polyethers as are obtainable by polymerization of tetrahydrofuran by means of cationic ring opening.

Useful polyether polyols likewise include the well-known addition products of styrene oxide, ethylene oxide, propylene oxide, butylene oxides and/or epichlorohydrin onto di- or polyfunctional starter molecules. Polyether polyols based on the at least proportional addition of ethylene oxide onto di- or polyfunctional starter molecules can also be used as component A4) (nonionic hydrophilicizing agents).

Useful starter molecules include all prior art compounds, for example water, butyl diglycol, glycerol, diethylene glycol, trimethylolpropane, propylene glycol, sorbitol, ethylenediamine, triethanolamine, 1,4-butanediol. Preferred starter molecules are water, ethylene glycol, propylene glycol, 1,4-butanediol, diethylene glycol and butyl diglycol.

Particularly preferred embodiments of the polyurethane dispersions (I) contain as component A2) a mixture of polycarbonate polyols and polytetramethylene glycol polyols, the proportion of polycarbonate polyols in this mixture being in the range from 20% to 80% by weight and the proportion of polytetramethylene glycol polyols in this mixture being in the range from 80% to 20% by weight. Preference is given to a proportion of 30% to 75% by weight for polytetramethylene glycol polyols and to a proportion of 25% to 70% by weight for polycarbonate polyols. Particular preference is given to a proportion of 35% to 70% by weight for polytetramethylene glycol polyols and to a proportion of 30% to 65% by weight for polycarbonate polyols, each subject to the proviso that the sum total of the weight percentages for the polycarbonate and polytetramethylene glycol polyols is 100% and the proportion of component A2) which is accounted for by the sum total of the polycarbonate and polytetramethylene glycol polyether polyols is at least 50% by weight, preferably 60% by weight and more preferably at least 70% by weight.

The compounds of component A3) have molecular weights of 62 and 400 g/mol.

A3) may utilize polyols of the specified molecular weight range with up to 20 carbon atoms, such as ethylene glycol, diethylene glycol, triethylene glycol, 1,2-propanediol, 1,3-propanediol, 1,4-butanediol, 1,3-butylene glycol, cyclohexanediol, 1,4-cyclohexanedimethanol, 1,6-hexanediol, neopentyl glycol, hydroquinone dihydroxyethyl ether, bisphenol A (2,2-bis(4-hydroxyphenyl)propane), hydrogenated bisphenol A, (2,2-bis(4-hydroxycyclohexyl)propane), trimethylolpropane, glycerol, pentaerythritol and also any desired mixtures thereof with one another.

Also suitable are ester diols of the specified molecular weight range such as α-hydroxybutyl-ε-hydroxycaproic acid ester, ω-hydroxyhexyl-γ-hydroxybutyric acid ester, β-hydroxyethyl adipate or bis(β-hydroxyethyl) terephthalate.

A3) may further utilize monofunctional isocyanate-reactive hydroxyl-containing compounds. Examples of such monofunctional compounds are ethanol, n-butanol, ethylene glycol monobutyl ether, diethylene glycol monomethyl ether, ethylene glycol monobutyl ether, diethylene glycol monobutyl ether, propylene glycol monomethyl ether, dipropylene glycol monomethyl ether, tripropylene glycol monomethyl ether, dipropylene glycol monopropyl ether, propylene glycol monobutyl ether, dipropylene glycol monobutyl ether, tripropylene glycol monobutyl ether, 2-ethylhexanol, 1-octanol, 1-dodecanol, 1-hexadecanol.

Preferred compounds for component A3) are 1,6-hexanediol, 1,4-butanediol, neopentyl glycol and trimethylolpropane.

An anionically or potentially anionically hydrophilicizing compound for component A4) is any compound which has at least one isocyanate-reactive group such as a hydroxyl group and also at least one functionality such as for example —COO$^-$M$^+$, —SO$_3^-$M$^+$, —PO(O$^-$M$^+$)$_2$ where M$^+$ is for example a metal cation, H$^+$, NH$_4^+$, NHR$_3^+$, where R in each occurrence may be $C_1$-$C_{12}$-alkyl, $C_5$-$C_6$-cycloalkyl and/or $C_2$-$C_4$-hydroxyalkyl, which functionality enters on interaction with aqueous media a pH-dependent dissociative equilibrium and thereby can have a negative or neutral charge. Useful anionically or potentially anionically hydrophilicizing compounds include mono- and dihydroxy carboxylic acids, mono- and dihydroxy sulphonic acids and also mono- and dihydroxy phosphonic acids and their salts. Examples of such anionic or potentially anionic hydrophilicizing agents are dimethylolpropionic acid, dimethylolbutyric acid, hydroxypivalic acid, malic acid, citric acid, glycolic acid, lactic acid and the propoxylated adduct formed from 2-butenediol and NaHSO$_3$ as described in DE-A 2 446 440, page 5-9, formula I-III. Preferred anionic or potentially anionic hydrophilicizing agents for component A4) are those of the aforementioned kind that have carboxylate or carboxyl groups and/or sulphonate groups.

Particularly preferred anionic or potentially anionic hydrophilicizing agents are those that contain carboxylate or carboxyl groups as ionic or potentially ionic groups, such as dimethylolpropionic acid, dimethylolbutyric acid and hydroxypivalic acid and salts thereof.

Useful nonionically hydrophilicizing compounds for component A4) include for example polyoxyalkylene ethers which contain at least one hydroxyl or amino group, preferably at least one hydroxyl group.

Examples are the monohydroxy-functional polyalkylene oxide polyether alcohols containing on average 5 to 70 and preferably 7 to 55 ethylene oxide units per molecule and obtainable in a conventional manner by alkoxylation of suitable starter molecules (for example in Ullmanns Encyclopädie der technischen Chemie, 4th edition, volume 19, Verlag Chemie, Weinheim pages 31-38).

These are either pure polyethylene oxide ethers or mixed polyalkylene oxide ethers, containing at least 30 mol % and preferably at least 40 mol % of ethylene oxide units, based on all alkylene oxide units present.

Preferred polyethylene oxide ethers of the aforementioned kind are monofunctional mixed polyalkylene oxide polyethers having 40 to 100 mol % of ethylene oxide units and 0 to 60 mol % of propylene oxide units.

Preferred nonionically hydrophilicizing compounds for component A4) include those of the aforementioned kind that are block (co)polymers prepared by blockwise addition of alkylene oxides onto suitable starters.

Useful starter molecules for such nonionic hydrophilicizing agents include saturated monoalcohols such as methanol, ethanol, n-propanol, isopropanol, n-butanol, isobutanol, sec-butanol, the isomers pentanols, hexanols, octanols and nonanols, n-decanol, n-dodecanol, n-tetradecanol, n-hexadecanol, n-octadecanol, cyclohexanol, the isomeric methylcyclohexanols or hydroxymethylcyclohexane, 3-ethyl-3-hydroxymethyloxetane or tetrahydrofurfuryl alcohol, diethylene glycol monoalkyl ethers, for example diethylene glycol monobutyl ether, unsaturated alcohols such as allyl alcohol, 1,1-dimethylallyl alcohol or oleic alcohol, aromatic alcohols such as phenol, the isomeric cresols or methoxyphenols, araliphatic alcohols such as benzyl alcohol, anis alcohol or cinnamyl alcohol, secondary monoamines such as dimethylamine, diethylamine, dipropylamine, diisopropylamine, dibutylamine, bis(2-ethylhexyl)amine, N-methylcyclohexylamine, N-ethylcyclohexylamine or dicyclohexylamine and also heterocyclic secondary amines such as morpholine, pyrrolidine, piperidine or 1H-pyrazole. Preferred starter molecules are saturated monoalcohols of the aforementioned kind. Particular preference is given to using diethylene glycol monobutyl ether or n-butanol as starter molecules.

Useful alkylene oxides for the alkoxylation reaction are in particular ethylene oxide and propylene oxide, which can be used in any desired order or else in admixture in the alkoxylation reaction.

Component B1) may utilize di- or polyamines such as 1,2-ethylenediamine, 1,2-diaminopropane, 1,3-diaminopropane, 1,4-diaminobutane, 1,6-diaminohexane, isophoronediamine, isomeric mixture of 2,2,4- and 2,4,4-trimethylhexamethylenediamine, 2-methylpentamethylenediamine, diethylene-triamine, triaminononane, 1,3-xylylenediamine, 1,4-xylylenediamine, α,α,α',α'-tetramethyl-1,3- and -1,4-xylylenediamine and 4,4-diaminodicyclohexylmethane and/or dimethylethylenediamine. It is also possible but less preferable to use hydrazine or and also hydrazides such as adipohydrazide.

Component B1) can further utilize compounds which as well as a primary amino group also have secondary amino groups or which as well as an amino group (primary or secondary) also have OH groups. Examples thereof are primary/secondary amines, such as diethanolamine, 3-amino-1-methylaminopropane, 3-amino-1-ethylaminopropane, 3-amino-1-cyclohexylaminopropane, 3-amino-1-methylaminobutane, alkanolamines such as N-aminoethylethanolamine, ethanolamine, 3-aminopropanol, neopentanolamine.

Component B1) can further utilize monofunctional isocyanate-reactive amine compounds, for example methylamine, ethylamine, propylamine, butylamine, octylamine, laurylamine, stearylamine, isononyloxypropylamine, dimethylamine, diethylamine, dipropylamine, dibutylamine, N-methylaminopropylamine, diethyl(methyl)aminopropylamine, morpholine, piperidine, or suitable substituted derivatives thereof, amide-amines formed from diprimary amines and monocarboxylic acids, monoketimes of diprimary amines, primary/tertiary amines, such as N,N-dimethylaminopropylamine.

Preferred compounds for component B1) are 1,2-ethylenediamine, 1,4-diaminobutane and isophoronediamine.

An anionically or potentially anionically hydrophilicizing compounds for component B2) is any compound which has at least one isocyanate-reactive group, preferably an amino group, and also at least one functionality such as for example —COO$^-$M$^+$, —SO$_3^-$M$^+$, —PO(O-M$^+$)$_2$ where M$^+$ is for example a metal cation, H$^+$, NH$_4^+$, NHR$_3^+$, where R in each occurrence may be $C_1$-$C_{12}$-alkyl, $C_5$-$C_6$-cycloalkyl and/or $C_2$-$C_4$-hydroxyalkyl radical which enters on interaction with aqueous media a pH-dependent dissociative equilibrium and thereby can have a negative or neutral charge.

Useful anionically or potentially anionically hydrophilicizing compounds are mono- and diamino carboxylic acids, mono- and diamino sulphonic acids and also mono- and diamino phosphonic acids and their salts. Examples of such anionic or potentially anionic hydrophilicizing agents are N-(2-aminoethyl)-β-alanine, 2-(2-aminoethylamino)ethanesulphonic acid, ethylenediaminepropylsulphonic acid, ethylenediaminebutylsulphonic acid, 1,2- or 1,3-propylenediamine-β-ethylsulphonic acid, glycine, alanine, taurine, lysine, 3,5-diaminobenzoic acid and the addition product of IPDA and acrylic acid (EP-A 0 916 647, Example 1). It is further possible to use cyclohexylaminopropanesulphonic acid (CAPS) from WO-A 01/88006 as anionic or potentially anionic hydrophilicizing agent.

Preferred anionic or potentially anionic hydrophilicizing agents for component B2) are those of the aforementioned kind that have carboxylate or carboxyl groups and/or sulphonate groups, such as the salts of N-(2-aminoethyl)-β-alanine, of 2-(2-aminoethylamino)ethanesulphonic acid or of the addition product of IPDA and acrylic acid (EP-A 0 916 647, Example 1).

Mixtures of anionic or potentially anionic hydrophilicizing agents and nonionic hydrophilicizing agents can also be used.

A preferred embodiment for producing the specific polyurethane dispersions utilizes components A1) to A4) and B1) to B2) in the following amounts, the individual amounts always adding up to 100% by weight:
5% to 40% by weight of component A1),
55% to 90% by weight of A2),
0.5% to 20% by weight of the sum total of components A3) and B1)
0.1% to 25% by weight of the sum total of the components component A4) and B2), with 0.1% to 5% by weight of anionic or potentially anionic hydrophilicizing agents from A4) and/or B2) being used, based on the total amount of components A1) to A4) and B1) to B2).

A particularly preferred embodiment for producing the specific polyurethane dispersions utilizes components A1) to A4) and B1) to B2) in the following amounts, the individual amounts always adding up to 100% by weight:
5% to 35% by weight of component A1),
60% to 90% by weight of A2),
0.5% to 15% by weight of the sum total of components A3) and B1)
0.1% to 15% by weight of the sum total of the components component A4) and B2), with 0.2% to 4% by weight of anionic or potentially anionic hydrophilicizing agents from A4) and/or B2) being used, based on the total amount of components A1) to A4) and B1) to B2).

A very particularly preferred embodiment for producing the specific polyurethane dispersions utilizes components A1) to A4) and B1) to B2) in the following amounts, the individual amounts always adding up to 100% by weight:
10% to 30% by weight of component A1),
65% to 85% by weight of A2),
0.5% to 14% by weight of the sum total of components A3) and B1)
0.1% to 13.5% by weight of the sum total of the components A4) and B2), with 0.5% to 3.0% by weight of anionic or potentially anionic hydrophilicizing agents from A4) and/or B2) being used, based on the total amount of components A1) to A4) and B1) to B2).

The production of the anionically hydrophilicized polyurethane dispersions (I) can be carried out in one or more stages in homogeneous phase or, in the case of a multistage reaction, partly in disperse phase. After completely or partially conducted polyaddition from A1) to A4) a dispersing, emulsifying or dissolving step is carried out. This is followed if appropriate by a further polyaddition or modification in disperse phase.

Any prior art process can be used, examples being the prepolymer mixing process, the acetone process or the melt dispersing process. The acetone process is preferred.

Production by the acetone process typically involves the constituents A2) to A4) and the polyisocyanate component A1) being wholly or partly introduced as an initial charge to produce an isocyanate-functional polyurethane prepolymer and optionally diluted with a water-miscible but isocyanate-inert solvent and heated to temperatures in the range from 50 to 120° C. The isocyanate addition reaction can be speeded using the catalysts known in polyurethane chemistry.

Useful solvents include the customary aliphatic, ketofunctional solvents such as acetone, 2-butanone, which can be added not just at the start of the production process but also later, optionally in portions. Acetone and 2-butanone are preferred.

Other solvents such as xylene, toluene, cyclohexane, butyl acetate, methoxypropyl acetate, N-methylpyrrolidone, N-ethylpyrrolidone, solvents having ether or ester units can additionally be used or wholly or partly distilled off or in the case of N-methylpyrrolidone, N-ethylpyrrolidone remain completely in the dispersion. But preference is given to not using any other solvents apart from the customary aliphatic, keto-functional solvents.

Subsequently, any constituents of A1) to A4) not added at the start of the reaction are added.

In the production of the polyurethane prepolymer from A1) to A4), the amount of substance ratio of isocyanate groups to isocyanate-reactive groups is in the range from 1.05 to 3.5, preferably in the range from 1.2 to 3.0 and more preferably in the range from 1.3 to 2.5.

The reaction of components A1) to A4) to form the prepolymer is effected partially or completely, but preferably completely. Polyurethane prepolymers containing free isocyanate groups are obtained in this way, without a solvent or in solution.

The neutralizing step to effect partial or complete conversion of potentially anionic groups into anionic groups utilizes bases such as tertiary amines, for example trialkylamines having 1 to 12 and preferably 1 to 6 carbon atoms and more preferably 2 to 3 carbon atoms in every alkyl radical or alkali metal bases such as the corresponding hydroxides.

Examples thereof are trimethylamine, triethylamine, methyldiethylamine, tripropylamine, N-methylmorpholine, methyldiisopropylamine, ethyldiisopropylamine and diisopropylethylamine. The alkyl radicals may also bear for example hydroxyl groups, as in the case of the dialkylmonoalkanol-, alkyldialkanol- and trialkanolamines. Useful neutralizing agents further include if appropriate inorganic bases, such as aqueous ammonia solution, sodium hydroxide or potassium hydroxide.

Preference is given to ammonia, triethylamine, triethanolamine, dimethylethanolamine or diisopropylethylamine and also sodium hydroxide and potassium hydroxide, particular preference being given to sodium hydroxide and potassium hydroxide.

The bases are employed in an amount of substance which is 50 and 125 mol % and preferably between 70 and 100 mol % of the amount of substance of the acid groups to be neutralized. Neutralization can also be effected at the same time as the dispersing step, by including the neutralizing agent in the water of dispersion.

Subsequently, in a further process step, if this has not already been done or only to some extent, the prepolymer obtained is dissolved with the aid of aliphatic ketones such as acetone or 2-butanone.

In the chain extension of stage B), $NH_2$— and/or NH-functional components are reacted, partially or completely, with the still remaining isocyanate groups of the prepolymer. Preferably, the chain extension/termination is carried out before dispersion in water.

Chain termination is typically carried out using amines B1) having an isocyanate-reactive group such as methylamine, ethylamine, propylamine, butylamine, octylamine, laurylamine, stearylamine, isononyloxypropylamine, dimethylamine, diethylamine, dipropylamine, dibutylamine, N-methylaminopropylamine, diethyl-(methyl)aminopropylamine, morpholine, piperidine or suitable substituted derivatives thereof, amide-amines formed from diprimary amines and mono-carboxylic acids, monoketimes of diprimary amines, primary/tertiary amines, such as N,N-dimethylaminopropylamine.

When partial or complete chain extension is carried out using anionic or potentially anionic hydrophilicizing agents conforming to definition B2) with NH$_2$ or NH groups, chain extension of the prepolymers is preferably carried out before dispersion.

The aminic components B1) and B2) can optionally be used in water- or solvent-diluted form in the process of the present invention, individually or in mixtures, any order of addition being possible in principle.

When water or organic solvent is used as a diluent, the diluent content of the chain-extending component used in B) is preferably in the range from 70% to 95% by weight.

Dispersion is preferably carried out following chain extension. For dispersion, the dissolved and chain-extended polyurethane polymer is either introduced into the dispersing water, if appropriate by substantial shearing, such as vigorous stirring for example, or conversely the dispersing water is stirred into the chain-extended polyurethane polymer solutions. It is preferable to add the water to the dissolved chain-extended polyurethane polymer.

The solvent still present in the dispersions after the dispersing step is then typically removed by distillation. Removal during the dispersing step is likewise possible.

The residual level of organic solvents in the polyurethane dispersions (I) is typically less than 1.0% by weight and preferably less than 0.5% by weight, based on the entire dispersion.

The pH of the polyurethane dispersions (I) which are essential to the present invention is typically less than 9.0, preferably less than 8.5, more preferably less than 8.0 and most preferably is in the range from 6.0 to 7.5.

The solids content of the polyurethane dispersions (I) is in the range from 40% to 70%, preferably in the range from 50% to 65% and more preferably in the range from 55% to 65% by weight.

The particular coagulants suitable for the polymeric dispersion or emulsion actually used are those known from the literature; they are familiar to a person skilled in the art.

Coagulant (II) can typically be any organic compound containing at least 2 cationic groups, preferably any known cationic flocculating and precipitating agent of the prior art, such as a cationic homo- or copolymer of a salt of poly[2-(N,N,N-trimethylamino)ethyl acrylate], of polyethyleneimine, of poly[N-(dimethylaminomethyl)acrylamide], of a substituted acrylamide, of a substituted methacrylamide, of N-vinylformamide, of N-vinylacetamide, of N-vinylimidazole, of 2-vinylpyridine or of 4-vinylpyridine.

Preferred cationic coagulants (II) are acrylamide copolymers comprising structural units of the general formula (2) and more preferably of the general formula (1) and (2)

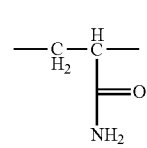
Formula (1)

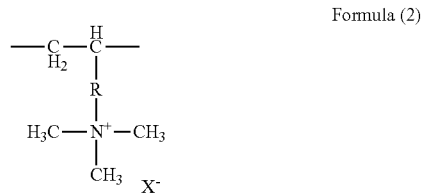
Formula (2)

where
R is C=O, —COO(CH$_2$)$_2$— or —COO(CH$_2$)$_3$— and
X$^-$ is a halide ion, preferably chloride.

The coagulants (II) preferably have number average molecular weights in the range from 500 000 to 50 000 000 g/mol.

Such coagulants (II) are marketed for example under the trade name of Praestol® (Degussa Stockhausen, Krefeld, Germany) as flocculants for activated sludges. Preferred coagulants of the Praestol® type are Praestol® K111L, K122L, K133L, BC 270L, K 144L, K 166L, BC 55L, 185K, 187K, 190K, K222L, K232L, K233L, K234L, K255L, K332L, K 333L, K 334L, E 125, E 150 and also mixtures thereof. Praestol® 185K, 187K and 190K and also mixtures thereof are very particularly preferred coagulating agents.

The residual levels of monomers, in particular acrylate and acrylamide monomers, in the coagulants are preferably less than 1% by weight, more preferably less than 0.5% by weight and most preferably less than 0.025% by weight.

The coagulants can be used in solid form or as aqueous solutions or dispersions. The use of aqueous dispersions or solutions is preferred.

As well as the polyurethane dispersions (I) and the coagulants (II), auxiliary and additive materials (III) can also be used.

Examples of such auxiliary and additive materials (III) are foam auxiliaries such as foam formers and stabilizers, thickeners or thixotroping agents, antioxidants, light stabilizers, emulsifiers, plasticizers, pigments, fillers and/or flow control agents.

Preferably, foam auxiliaries such as foam formers and stabilizers are included as auxiliary and additive materials (III). Useful foam auxiliaries include commercially available compounds such as fatty acid amides, sulphosuccinamides hydrocarbyl sulphates or sulphonates or fatty acid salts, in which case the lipophilic radical preferably contains 12 to 24 carbon atoms.

Preferred foam auxiliaries are alkanesulphonates or alkane sulphates having 12 to 22 carbon atoms in the hydrocarbyl radical, alkylbenzenesulphonates or alkylbenzene sulphates having 14 to 24 carbon atoms in the hydrocarbyl radical or fatty acid amides or fatty acid salts having 12 to 24 carbon atoms.

Such fatty acid amides are preferably based on mono- or di(C$_2$-C$_3$-alkanol)amines. The fatty acid salts may be for example alkali metal salts, amine salts or unsubstituted ammonium salts.

Such fatty acid derivatives are typically based on fatty acids such as lauric acid, myristic acid, palmitic acid, oleic acid, stearic acid, ricinoleic acid, behenic acid or arachidic acid, coco fatty acid, tallow fatty acid, soya fatty acid and their hydrogenation products.

Particularly preferred foam auxiliaries are mixtures of sulphosuccinamides and ammonium stearates, these preferably containing 20% to 60% by weight and more preferably 30% to 50% by weight of ammonium stearates and preferably 80% to 40% by weight and more preferably 70% to 50% by weight of sulphosuccinamides.

Commercially available thickeners can be used, such as derivatives of dextrin, of starch or of cellulose, examples being cellulose ethers or hydroxyethylcellulose, organic wholly synthetic thickeners based on polyacrylic acids, polyvinylpyrrolidones, poly(meth)acrylic compounds or polyurethanes (associative thickeners) and also inorganic thickeners, such as bentonites or silicas.

In principle, although not preferably, the compositions which are essential to the present invention can also contain crosslinkers such as unblocked polyisocyanates, amide- and amine-formaldehyde resins, phenolic resins, aldehydic and ketonic resins, examples being phenol-formaldehyde resins, resols, furan resins, urea resins, carbamic ester resins, triazine resins, melamine resins, benzoguanamine resins, cyanamide resins or aniline resins.

The compositions which are essential to the present invention typically contain, based on dry substance, 80 to 99.5 parts by weight of dispersion (I), 0.5 to 5 parts by weight of cationic coagulant (II), 0 to 10 parts by weight of foam auxiliary, 0 to 10 parts by weight of crosslinker and 0% to 10% by weight of thickener.

Preferably, the compositions which are essential to the present invention contain, based on dry substance, 85 to 97 parts by weight of dispersion (I), 0.75 to 4 parts by weight of cationic coagulant (II), 0.5 to 6 parts by weight of foam auxiliary, 0 to 5 parts by weight of crosslinker and 0% to 5% by weight of thickener.

More preferably, the compositions which are essential to the present invention contain, based on dry substance, 89 to 97 parts by weight of dispersion (I), 0.75 to 3 parts by weight of cationic coagulant (II), 0.5 to 5 parts by weight of foam auxiliary, 0 to 4 parts by weight of crosslinker and 0 to 4 parts by weight of thickener.

As well as components (I), (II) and if appropriate (III), other aqueous binders can also be used in the compositions which are essential to the present invention. Such aqueous binders can be constructed for example of polyester, polyacrylate, polyepoxy or other polyurethane polymers. Similarly, the combination with radiation-curable binders as described for example in EP-A-0 753 531 is also possible. It is further possible to employ other anionic or nonionic dispersions, such as polyvinyl acetate, polyethylene, polystyrene, polybutadiene, polyvinyl chloride, polyacrylate and copolymer dispersions.

Frothing in the process of the present invention is accomplished by mechanical stirring of the composition at high speeds of rotation or by decompressing a blowing gas.

Mechanical frothing can be effected using any desired mechanical stirring, mixing and dispersing techniques. Air is generally introduced, but nitrogen and other gases can also be used for this purpose.

The foam thus obtained is, in the course of frothing or immediately thereafter, applied to a substrate or introduced into a mould and dried.

Application to a substrate can be for example by pouring or blade coating, but other conventional techniques are also possible. Multilayered application with intervening drying steps is also possible in principle.

A satisfactory drying rate for the foams is observed at a temperature as low as 20° C., so that drying on injured human or animal tissue presents no problem. However, temperatures above 30° C. are preferably used for more rapid drying and fixing of the foams. However, drying temperatures should not exceed 200° C., preferably 150° C. and more preferably 130° C., since undesirable yellowing of the foams can otherwise occur, inter alia. Drying in two or more stages is also possible.

The polymeric dispersion or emulsion used according to the invention may additionally contain, or be additized, with physiologically active entities in effective amounts. The biomedical foam articles of the present invention may contain for example local anaesthetics, enzymes, antibacterial or fungicidal actives or hormonal compounds.

Preferably, the polymeric dispersion or emulsion used according to the present invention contains at least one active component selected from the group of antiseptics, growth factors, protease inhibitors and non-steroidal anti-inflammatories/opiates.

The biomedical foam articles of the present invention are particularly useful for treating skin wounds, in particular chronic wounds such as diabetic, venous, decubitus ulcers, but also burn wounds and acute wounds, in particular minimally acute wounds.

They ensure complete and accurately fitted packing of the wound in the depth dimension as well as the other dimensions, exhibit rapid curing and good imbibition of liquid and are simple to handle.

EXAMPLES

Unless indicated otherwise, all percentages are by weight.

Solids contents were determined in accordance with DIN-EN ISO 3251.

NCO contents were unless expressly mentioned otherwise determined volumetrically in accordance with DIN-EN ISO 11909.

Substances and Abbreviations Used:

Diaminosulphonate: $NH_2$—$CH_2CH_2$—$NH$—$CH_2CH_2$—$SO_3Na$ (45% in water)

Desmophen® C2200: polycarbonate polyol, OH number 56 mg KOH/g, number average molecular weight 2000 g/mol (Bayer MaterialScience AG, Leverkusen, Germany)

PolyTHF® 2000: polytetramethylene glycol polyol, OH number 56 mg KOH/g, number average molecular weight 2000 g/mol (BASF AG, Ludwigshafen, Germany)

PolyTHF® 1000: polytetramethylene glycol polyol, OH number 112 mg KOH/g, number average number average molecular weight 1000 g/mol (BASF AG, Ludwigshafen, Germany)

LB 25 polyether: monofunctional polyether based on ethylene oxide/propylene oxide, number average molecular weight 2250 g/mol, OH number 25 mg KOH/g (Bayer MaterialScience AG, Leverkusen, Germany)

Stokal® STA: foam auxiliary based on ammonium stearate, active content: 30% (Bozzetto GmbH, Krefeld, Germany)

Stokal® SR: foam auxiliary based on succinamate, active content: about 34% (Bozzetto GmbH, Krefeld, Germany)

Simulsol® SL 26: alkylpolyglycoside based on dodecyl alcohol, about 52% in water, Seppic GmbH, Cologne, Germany Praestol® 185 K: cationic flocculation auxiliary containing the structures of formulae (1) and (2), solids content 25% by weight (Degussa AG, Germany)

The determination of the average particle sizes (the number average is reported) of the polyurethane dispersions (I) was carried out using laser correlation spectroscopy (instrument: Malvern Zetasizer 1000, Malver Inst. Limited).

Example 1

Polyurethane Dispersion 1

987.0 g of PolyTHF® 2000, 375.4 g of PolyTHF® 1000, 761.3 g of Desmophen® C2200 and 44.3 g of LB 25 polyether were heated to 70° C. in a standard stirring apparatus. Then, a mixture of 237.0 g of hexamethylene diisocyanate and 313.2 g of isophorone diisocyanate was added at 70° C. in the course of 5 min and the mixture was stirred at 120° C. until the theoretical NCO value was reached or the actual NCO value was slightly below the theoretical NCO value. The ready-produced prepolymer was dissolved with 4830 g of acetone and, in the process, cooled down to 50° C. and subsequently admixed with a solution of 25.1 g of ethylenediamine, 116.5 g of isophoronediamine, 61.7 g of diaminosulphonate and 1030 g of water metered in over 10 min. The mixture was subsequently stirred for 10 min. Then, a dispersion was formed by addition of 1250 g of water. This was followed by removal of the solvent by distillation under reduced pressure.

The white dispersion obtained had the following properties:
Solids content: 61%
Particle size (LKS): 312 nm
Viscosity (viscometer, 23° C.): 241 mPas
pH (23° C.): 6.02

Example 2

Polyurethane Dispersion 2

223.7 g of PolyTHF® 2000, 85.1 g of PolyTHF® 1000, 172.6 g of Desmophen® C2200 and 10.0 g of LB 25 polyether were heated to 70° C. in a standard stirring apparatus. Then, a mixture of 53.7 g of hexamethylene diisocyanate and 71.0 g of isophorone diisocyanate was added at 70° C. in the course of 5 min and the mixture was stirred at 120° C. until the theoretical NCO value was reached or the actual NCO value was slightly below the theoretical NCO value. The ready-produced prepolymer was dissolved with 1005 g of acetone and, in the process, cooled down to 50° C. and subsequently admixed with a solution of 5.70 g of ethylenediamine, 26.4 g of isophoronediamine, 9.18 g of diaminosulphonate and 249.2 g of water metered in over 10 min. The mixture was subsequently stirred for 10 min. Then, a dispersion was formed by addition of 216 g of water. This was followed by removal of the solvent by distillation under reduced pressure.

The white dispersion obtained had the following properties:
Solids content: 63%
Particle size (LKS): 495 nm
Viscosity (viscometer, 23° C.): 133 mPas
pH (23° C.): 6.92

Example 3

Polyurethane Dispersion 3

987.0 g of PolyTHF® 2000, 375.4 g of PolyTHF® 1000, 761.3 g of Desmophen® C2200 and 44.3 g of LB 25 polyether were heated to 70° C. in a standard stirring apparatus. Then, a mixture of 237.0 g of hexamethylene diisocyanate and 313.2 g of isophorone diisocyanate was added at 70° C. in the course of 5 min and the mixture was stirred at 120° C. until the theoretical NCO value was reached or the actual NCO value was slightly below the theoretical NCO value. The ready-produced prepolymer was dissolved with 4830 g of acetone and, in the process, cooled down to 50° C. and subsequently admixed with a solution of 36.9 g of 1,4-diaminobutane, 116.5 g of isophoronediamine, 61.7 g of diaminosulphonate and 1076 g of water metered in over 10 min. The mixture was subsequently stirred for 10 min. Then, a dispersion was formed by addition of 1210 g of water. This was followed by removal of the solvent by distillation under reduced pressure.

The white dispersion obtained had the following properties:
Solids content: 59%
Particle size (LKS): 350 nm
Viscosity (viscometer, 23° C.): 126 mPas
pH (23° C.): 7.07

Example 4

Polyurethane Dispersion 4

201.3 g of PolyTHF® 2000, 76.6 g of PolyTHF® 1000, 155.3 g of Desmophen® C2200, 2.50 g of 1,4-butanediol and 10.0 g of LB 25 polyether were heated to 70° C. in a standard stirring apparatus. Then, a mixture of 53.7 g of hexamethylene diisocyanate and 71.0 g of isophorone diisocyanate was added at 70° C. in the course of 5 min and the mixture was stirred at 120° C. until the theoretical NCO value was reached or the actual NCO value was slightly below the theoretical NCO value. The ready-produced prepolymer was dissolved with 1010 g of acetone and, in the process, cooled down to 50° C. and subsequently admixed with a solution of 5.70 g of ethylenediamine, 26.4 g of isophoronediamine, 14.0 g of diaminosulphonate and 250 g of water metered in over 10 min. The mixture was subsequently stirred for 10 min. Then, a dispersion was formed by addition of 243 g of water. This was followed by removal of the solvent by distillation under reduced pressure.

The white dispersion obtained had the following properties:
Solids content: 62%
Particle size (LKS): 566 nm
Viscosity (viscometer, 23° C.): 57 mPas
pH (23° C.): 6.64

Example 5

Polyurethane Dispersion 5

201.3 g of PolyTHF® 2000, 76.6 g of PolyTHF® 1000, 155.3 g of Desmophen® C2200, 2.50 g of trimethylolpropane and 10.0 g of LB 25 polyether were heated to 70° C. in a standard stirring apparatus. Then, a mixture of 53.7 g of hexamethylene diisocyanate and 71.0 g of isophorone diisocyanate was added at 70° C. in the course of 5 min and the mixture was stirred at 120° C. until the theoretical NCO value was reached or the actual NCO value was slightly below the theoretical NCO value. The ready-produced prepolymer was dissolved with 1010 g of acetone and, in the process, cooled down to 50° C. and subsequently admixed with a solution of 5.70 g of ethylenediamine, 26.4 g of isophoronediamine, 14.0 g of diaminosulphonate and 250 g of water metered in over 10 min. The mixture was subsequently stirred for 10 min. Then, a dispersion was formed by addition of 293 g of water. This was followed by removal of the solvent by distillation under reduced pressure.

The white dispersion obtained had the following properties:
Solids content: 56%
Particle size (LKS): 440 nm
Viscosity (viscometer, 23° C.): 84 mPas
pH (23° C.): 6.91

Example 6

Polyurethane Dispersion 6

1072 g of PolyTHF® 2000, 407.6 g of PolyTHF® 1000, 827 g of Desmophen® C2200 and 48.1 g of LB 25 polyether were heated to 70° C. in a standard stirring apparatus. Then, a mixture of 257.4 g of hexamethylene diisocyanate and 340 g of isophorone diisocyanate was added at 70° C. in the course of 5 min and the mixture was stirred at 120° C. until the theoretical NCO value was reached or the actual NCO value was slightly below the theoretical NCO value. The ready-produced prepolymer was dissolved with 4820 g of acetone and, in the process, cooled down to 50° C. and subsequently admixed with a solution of 27.3 g of ethylenediamine, 126.5 g of isophoronediamine, 67.0 g of diaminosulphonate and 1090 g of water metered in over 10 min. The mixture was subsequently stirred for 10 min. Then, a dispersion was formed by addition of 1180 g of water. This was followed by removal of the solvent by distillation under reduced pressure.

The white dispersion obtained had the following properties:
Solids content: 60%
Particle size (LKS): 312 nm
Viscosity (viscometer, 23° C.): 286 mPas
pH (23° C.): 7.15

Examples 7-12

Foams Produced from the Polyurethane Dispersions of Examples 1-6

The Table 1 amounts of the polyurethane dispersions produced as described in Examples 1-6 were mixed with the foam auxiliaries indicated in Table 1 and frothed by means of a commercially available hand stirrer (stirrer made of bent wire) to a 1 litre foam volume. While stirring was continued, the foams obtained were finally coagulated by addition of Praestol® 185 K; coagulation left foam volume unchanged (slight increase in viscosity). Thereafter, the foams were drawn down on silicone-coated paper by means of a blade coater set to the gap height reported in Table 1. Table 1 similarly recites the drying conditions for the foams produced as indicated. Clean white foams having good mechanical properties and a fine structure of pores were obtained without exception.

TABLE 1

| Foam No. | Polyurethane dispersion (Example) | Stokal® STA | Stokal® SR | Praestol® 185 k | SH[1] [mm] | Curing |
|---|---|---|---|---|---|---|
| 1a | 235.0 (1) | 4.2 | 5.6 | 5.0 | 2 | 2 h/37° C. |
| 1b | 235.0 (1) | 4.2 | 5.6 | 5.0 | 4 | 18 h/37° C. |
| 1c | 235.0 (2) | 4.2 | 5.6 | 5.0 | 6 | 18 h/37° C. |
| 1d | 235.0 (2) | 4.2 | 5.6 | 5.0 | 4 | 18 h/37° C., 30 min/120° C. |
| 1e | 235.0 (2) | 4.2 | 5.6 | 5.0 | 6 | 18 h/37° C., 30 min/120° C. |
| 2 | 235.0 (2) | 4.2 | 5.6 | 5.0 | 4 | 2 h/37° C., 30 min/120° C. |
| 3 | 235.0 (3) | 4.2 | 5.6 | 5.0 | 4 | 18 h/37° C. |
| 4 | 235.0 (4) | 4.2 | 5.6 | 5.0 | 4 | 2 h/37° C., 30 min/120° C. |
| 5 | 235.0 (5) | 4.2 | 5.6 | 5.0 | 4 | 2 h/37° C., 30 min/120° C. |
| 6 | 235.0 (6) | 4.2 | 5.6 | 5.0 | 4 | 2 h/37° C., 30 min/120° C. |

[1]blade coater gap height

As is discernible from Table 2, all the foams exhibited a very rapid imbibition of water, a high absorbence of physiological saline ("free swell absorbency"), a very high moisture vapour transmission rate (MVTR) and also good mechanical strength, in particular after moist storage.

TABLE 2

| Foam No. | Imbibition rate[1] [s] | Free absorbency[2] [g/10 cm$^2$] | MVTR[3] [g/m$^2$*24 h] |
|---|---|---|---|
| 1a | not determined | 13.4 | 6500 |
| 1b | not determined | 23.6 | 6300 |
| 1c | not determined | 33.0 | 5100 |
| 1d | 9 | 20.1 | 4400 |
| 1e | 9 | 29.6 | 4200 |
| 2 | 7 | 21.4 | 4100 |
| 3 | 7 | 23.4 | 3700 |
| 4 | 18 | 20.2 | 4100 |
| 5 | 11 | 25.8 | 4300 |
| 6 | 17 | 22.1 | 4400 |

[1]time for complete penetration of a drop of distilled water into the foam (test on side facing the paper);
[2]absorption of physiological saline determined according to DIN EN 13726-1 Part 3.2 (5 instead of 9 test samples);
[3]moisture vapour transition rate determined according to DIN EN 13726-2 Part 3.2

Example 13

54 g of a polyurethane dispersion prepared according to Example 2 were mixed with 1.37 g of Simulsol® SL 26. This mixture was introduced into a chamber of a suitable 2-component aerosol can; the other chamber was filled with 1.69 g of Praestol® 185 K. The components were finally admixed with 6 g of a blowing agent mixture of i-butane/propane/n-butane. After spraying (about 1 cm wet film thickness) and drying at ambient conditions, a clean white, fine-cell foam was obtained.

The invention claimed is:

1. A method for treating a wound comprising spraying a composition comprising at least one ionic polyurethane dispersion or emulsion and also at least one coagulant directly onto skin to form a biomedical foam article, wherein the composition ensures a complete and accurate fitted packing of the wound by forming a three-dimensional body which conforms to the spatial shape of the wound and covers the wound surface.

2. A method according to claim 1, wherein the ionic polyurethane dispersion or emulsion is selected from the group consisting of aqueous polyurethane dispersions, aliphatic polyurethane dispersions and polyurethane hybrid emulsions.

3. A method according to claim 1, wherein the ionic polyurethane dispersion or emulsion is an aqueous anionic hydrophilic polyurethane dispersion.

4. A method according to claim 1, wherein the ionic polyurethane dispersion or emulsion is an aqueous anionic hydrophilic polyurethane dispersion obtainable by
A) isocyanate-functional prepolymers being prepared from
A1) organic polyisocyanates
A2) polymeric polyols having number average molecular weights in the range from 400 to 8000 g/mol, and OH functionalities in the range from 1.5 to 6, and
A3) optionally hydroxyl-functional compounds having molecular weights in the range from 62 to 399 g/mol, and
A4) optionally isocyanate-reactive, anionic or potentially anionic and/or optionally nonionic hydrophilicizing agents,
and
B) isocyanate-functional prepolymers free NCO groups then being wholly or partly reacted
B1) optionally with amino-functional compounds having molecular weights in the range from 32 or 400 g/mol, and
B2) with isocyanate-reactive, anionic or potentially anionic hydrophilicizing agents
by chain extension, and the prepolymers being dispersed in water before, during or after step B), any potentially ionic groups present being converted into the ionic form by partial or complete reaction with a neutralizing agent.

5. A method according to claim 4, wherein the aqueous, anionically hydrophilicized polyurethane dispersions are prepared using in A1) 1,6-hexamethylene diisocyanate, isophorone diisocyanate, the isomeric bis(4,4'-isocyanatocyclohexyl)methanes, or mixtures thereof, and in A2) a mixture of polycarbonate polyols and polytetramethylene glycol polyols, the proportion of component A2) which is contributed by the sum total of the polycarbonate and polytetramethylene glycol polyether polyols being at least 70% by weight.

6. A method according to claim 1, wherein the coagulant is an acrylamide copolymer comprising structural units of formula (1) and (2)

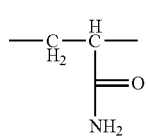

Formula (1)

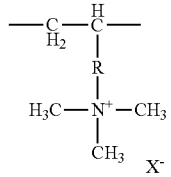

Formula (2)

where
R is C=O, —COO(CH$_2$)$_2$ or —COO(CH$_2$)$_3$, and
X is a halide ion.

7. A method according to claim 1, wherein the ionic polyurethane dispersion or emulsion additionally comprises at least one active component selected from the group consisting of antiseptics, growth factors, protease inhibitors and non-steroidal anti-inflammatories and opiates.

8. A process for producing a biomedical foam article comprising spraying a composition comprising at least one ionic polyurethane dispersion or emulsion and also at least one coagulant and also, optionally, at least one active component selected from the group consisting of antiseptics, growth factors, protease inhibitors and non-steroidal anti-inflammatories and opiates directly onto a wound.

9. A method according to claim 1, wherein the wound is a chronic wound.

10. A method according to claim 4, wherein A3) is present and is 1,6-hexanediol, 1,4-butanediol, neopentyl glycol or trimethylolpropane.

11. A method according to claim 4, wherein B1) is present and is 1,2-ethylenediamine, 1,4-diaminobutaine or isophoronediamine.

12. A method according to claim 4, wherein the aqueous anionically hydrophilicized polyurethane dispersion is 5% to 40% by weight of component A1), 55% to 90% by weight of A2), 0.5% to 20% by weight of the sum total of components A3) and B1), and 0.1% to 25% by weight of the sum total of the components A4) and B2), with 0.1% to 5% by weight of anionic or potentially anionic hydrophilicizing agents from A4) and/or B2) being used, based on the total amount of components A1) to A4) and B1) to B2).

13. A method according to claim 1, wherein the ionic polyurethane dispersion or emulsion is an ionic polyurethane dispersion in which solids content is from 40% to 70% by weight.

14. A method according to claim 1, wherein the composition additionally comprises one or more foam auxillary, thickener or thixotroping agent, antioxidant, light stabilizer, emulsifier, plasticizer, pigment, filler, flow-control agent, crosslinker.

15. A method according to claim 14, wherein the composition is 80 to 99.5 parts by weight of ionic polymeric dispersion, 0.5 to 5 parts by weight of coagulant, 0 to 10 parts by weight of foam auxiliary, 0 to 10 parts by weight of crosslinker, and 0% to 10% by weight of thickener.

16. The method according to claim 1 wherein the biomedical foam article comprises a porous material having at least some open-cell content and needing not more than five minutes to cure from a liquid form into a solid foam article.

17. The method according to claim 1 wherein the biomedical foam article comprises a physiological saline absorbence of 100 to 2500%.

18. The method according to claim 1, wherein the biomedical foam article comprises a water vapour transmission rate of 2000 to 12 000 g/m$^2$ per 24 h.

* * * * *